United States Patent
Park

(10) Patent No.: US 9,180,048 B2
(45) Date of Patent: Nov. 10, 2015

(54) EYE SHAPE MODIFICATION SYSTEMS

(71) Applicant: Robert Park, Asheville, NC (US)

(72) Inventor: Robert Park, Asheville, NC (US)

(*) Notice: Subject to any disclaimer, the term of this patent is extended or adjusted under 35 U.S.C. 154(b) by 107 days.

(21) Appl. No.: 14/022,057

(22) Filed: Sep. 9, 2013

(65) Prior Publication Data

US 2014/0074128 A1 Mar. 13, 2014

Related U.S. Application Data

(60) Provisional application No. 61/698,332, filed on Sep. 7, 2012.

(51) Int. Cl.
*A61F 2/14* (2006.01)
*A61F 9/007* (2006.01)
*A61K 9/00* (2006.01)
*A61F 9/00* (2006.01)

(52) U.S. Cl.
CPC ............. *A61F 9/00727* (2013.01); *A61F 2/147* (2013.01); *A61K 9/0051* (2013.01); *A61F 9/0017* (2013.01)

(58) Field of Classification Search
USPC .......................................................... 623/4.1
See application file for complete search history.

(56) References Cited

U.S. PATENT DOCUMENTS

| | | | |
|---|---|---|---|
| 4,549,529 A | 10/1985 | White | |
| 4,851,003 A | 7/1989 | Lindstrom | |
| 4,880,017 A | 11/1989 | Soll et al. | |
| 4,907,586 A | 3/1990 | Bille et al. | |
| 4,961,744 A | 10/1990 | Kilmer et al. | |
| 4,976,719 A | 12/1990 | Siepser | |
| 5,006,123 A | 4/1991 | Soll et al. | |
| 5,188,125 A | 2/1993 | Kilmer et al. | |
| 5,300,118 A | 4/1994 | Silvestrini et al. | |
| 5,354,331 A | 10/1994 | Schachar | |
| 5,489,299 A | 2/1996 | Schachar | |
| 5,503,165 A | 4/1996 | Schachar | |
| 5,529,076 A | 6/1996 | Schachar | |
| 5,722,952 A | 3/1998 | Schachar | |
| 6,117,170 A | 9/2000 | Batdorf, Sr. | |
| 6,511,508 B1 | 1/2003 | Shahinpoor et al. | |
| 6,547,714 B1 | 4/2003 | Dailey | |
| 7,037,336 B2 | 5/2006 | Ward | |
| 7,316,676 B2 | 1/2008 | Peyman et al. | |
| 7,736,389 B1 | 6/2010 | Damiano | |
| 2003/0139808 A1 | 7/2003 | Shahinpoor et al. | |
| 2004/0098126 A1 | 5/2004 | Freeman et al. | |
| 2006/0167422 A1 | 7/2006 | Shahinpoor et al. | |
| 2010/0305694 A1 | 12/2010 | Lee et al. | |

OTHER PUBLICATIONS

Ward et al.; "The efficacy and safety of posterior pole buckles in the control of progressive high myopia"; Eye (2009) 23, 2169-2174; published online Feb. 20, 2009.
Robert C. Watcke M.D.; "Notes, Cases, Instruments: An Encircling Element Connection for Scleral Buckling Procedures"; 989-91, Jun. 1998.

*Primary Examiner* — David H Willse
*Assistant Examiner* — Javier Blanco

(57) ABSTRACT

An eye shape modification (ESM) system such as a scleral buckle featuring a band having a first end, a second end opposite the first end, and a first side; and a fixation zone disposed on the first side of the band. The fixation zone is adapted to accept sutures and can be sutured to a scleral surface. The ESM system may also feature a closure system for closing the two ends of the band together. The ESM system may also feature a calibrated shortening mechanism allowing a calibrated reduction in circumference and diameter.

14 Claims, 26 Drawing Sheets

162

168
110

Enlarged View of Forward Connection Zone (8 indents)

Thickness= 0.75mm

EYE SHAPE MODIFICATION SYSTEMS

CROSS REFERENCE

This application claims priority to U.S. Patent Application No. 61/698,332 filed Sep. 7, 2012, the specification(s) of which is/are incorporated herein in their entirety by reference.

FIELD OF THE INVENTION

The present invention relates to methods and devices for modifying eye shape, more particularly to scleral buckles.

BACKGROUND OF THE INVENTION

Rhegmatogenous retinal detachment (RRD) is a potentially blinding disease that affects 1 in 10,000 people. Rhegmatogenous retinal detachments generally develop in eyes in a two-step fashion. First, excess traction on the retina from the vitreous gel inside the eye causes a retinal tear. Second, persistent traction on a retinal tear allows vitreous fluid to track underneath the retina, causing a separation of the photoreceptor layer from the underlying retinal pigment epithelium. Generally, if a rhegmatogenous retinal detachment is left untreated blindness occurs.

Myopia, or nearsightedness, is a disease in which images are focused on a point inside the eye rather than being focused on the retina. Hyperopia, or farsightedness, is a disease in which light is focused on a point behind the eye rather than on the retina. In both cases, either the focusing power of the cornea/lens combination is not appropriate for the eye length. The abnormality may lie with the size of the eye itself or may lie with the power of the cornea/lens power.

Myopia is a condition in which the power of the focusing system, e.g., cornea and lens, are too strong for the globe length, or the globe is unusually large. Hyperopia is a condition in which the eye is too short, or the power of the focusing system is too weak.

Globe size and RRD are related. Patients with enlarged eyes, i.e., myopes, are at increased risk of developing RRDs, and a number of biomechanical factors contribute to the development. Patients with hyperopia have small eyes and have a decreased risk of RRD.

Without wishing to limit the present invention to any theory or mechanism, current model of RRD implicates vitreo-retinal traction as the primary cause of retinal detachment. According to the model, vitreo-retinal traction induces a retinal tear and persistent traction causes separation of the photoreceptors from the underlying RPE cells. Vitreous fluid overwhelms the RPE pump and a RRD ensues.

The process by which retinal detachment occurs is well documented clinically and experimentally. Thompson, through his classic series of experiments on RRD, has clearly demonstrated the importance of vitreo-retinal traction in the development of RRD. Recently, data regarding the overall shapes and dimensions of eyes in emmetropia and myopia has been determined in vivo by surface coil MRI scanning. This new information can help us to understand which eyes are at greatest risk for retinal detachment and how to repair them.

Biomechanically, the insults causing a RRD may be divided into two events: the retinal tear and the actual separation of the retina from the RPE. Biomechanically, the retinal tear is no different than failure of any other structure. Failure or fracture of a structure occurs when the stress (defined as the force/cross sectional area) in the structure is high enough to overcome the inherent strength of a material.

Increased intraretinal stress can also lead to tearing of the retina. The stress can be from vitreo-retinal traction but it can also come from other sources. Intrinsic intraretinal stress depends on the retinal thickness and eye shape and is guided by Laplace's Law. LaPlace's Law essentially states that at a constant intraocular pressure, as the radius of the eye increases, the wall tension or force in the wall increases. Thus, increasing the radius of the eye increases the intraretinal stress. Thinner retinas also have increased intraretinal stress because the inherent wall tension must be carried by a smaller cross sectional area.

As we look at Atchison's MRI data regarding myopic eyes, we can understand the impact of myopic eye dimensions on intraretinal stress. Myopic globes are, in order of magnitude, longer, taller, and wider than emmetropic eyes. Myopic globes have thinner retinas horizontally but not vertically than emmetropic globes. The result of the dimensional differences is that intraretinal stress increases with increased myopia in the vertical and horizontal dimensions.

With a higher baseline intraretinal stress, less force is required to tear the retina when vitreo-retinal traction is applied. We can see why myopes have a higher risk of retinal tear when exposed to vitreo-retinal traction.

The second component in generation of retinal detachments is increased vitreoretinal traction. From Atchison's data, we know that myopic globes are, in order of magnitude longer, taller and wider than emmetropes. Although the resultant vitreo-retinal traction is difficult to quantify, we can make the following generalizations regarding the effect of globe dimensions on vitreo-retinal traction: (1) axial traction is the greatest which may be a contributing cause of early posterior vitreous detachment; (2) vertical traction is next most significant; and (3) horizontal traction is also increased, contributing to increased intraretinal stress, tearing and retinal detachments. The increased vitreoretinal traction when combined with increased intrinsic intraretinal stress and gravity makes retinal tears and RRD more likely in myopes.

The treatment of RRD may be accomplished via pars plana vitrectomy, via pneumatic retinopexy, or via a scleral buckle. In pars plana vitrectomy, three small incisions are made in the eye and the vitreous gel is dissected and removed from the eye to relieve the vitreo-retinal traction. Fluid may be drained from under the retina. The retinal tear is treated with laser photocoagulation or cryoretinopexy to induce scarring seal the hole in the retina. A gas tamponade may be used to close the retinal hole and stabilize the retina while the hole heals. In pneumatic retinopexy, a gas bubble is placed in the eye to block fluid from entering the retinal hole. The retinal tear is treated with laser photocoagulation or cryoretinopexy to induce permanent closure of the tear.

Generally, in scleral buckling, the conjunctiva and the Tenon's capsule are dissected from the sclera and a scleral buckling element (e.g.; see FIG. 1A), usually a piece of inert plastic or silicone rubber, solid or sponge, is used to indent the eye. The scleral buckle element may be sutured into place directly or may be held in place with an encircling band (imagine a belt wrapped around a volleyball). The indentation closes the hole created by the retinal tear and allows re-absorption of fluid from under the retina and resolution of the RRD. The edges of the retinal tear are treated with laser photocoagulation or cryoretinopexy to permanently seal the tear. A gas bubble may or may not be used to further seal the tear from an interior approach and subretinal fluid may or may not be removed through the sclera.

In the scleral buckle procedure, when an encircling band is used to either hold a scleral buckle in place or is used to close a hole without an additional scleral buckle element, at least one horizontal mattress suture is used in each oblique quadrant to form a belt loop in which the encircling band sits. Placement of the sutures, especially the posterior sutures, is the most difficult and risky part of the scleral buckling procedure. If the suture is not placed properly, the scleral buckle will not indent the eye at the right place, the tear will not be closed, and the retinal will not reattach. There is also risk with the placement of sclera sutures as the globe may be perforated during the suturing process. Perforation can lead to additional retinal holes and further detachment, or may result in severe hemorrhaging from the choroidal circulation with resultant scarring and possible blindness. Once the encircling band is placed around the eye, the two ends are attached to each other usually with a ring of silicone rubber. Tightening the band, like tightening a belt, decreases the circumference of the eye and causes indentation of the eye. Surgeons currently adjust tightness of the encircling band (and thus amount of indentation) manually, using experience and surgical judgment rather than any quantitated system. Knowing how much to tighten an encircling band is the second most difficult and time consuming part of the scleral buckle procedure.

Scleral buckles have a number of biomechanical effects on the eye. Specifically, a moderate height-encircling band reduces the ocular circumference and diameter, normalizes the shape of the globe (making it more round), and reverses the force vector of epiretinal membranes. The net effect is a reduction in both the intraretinal stress and vitreoretinal traction (drivers of RRD). Without wishing to limit the present invention to any theory or mechanism, it is believed that caution must be taken though in the degree of indentation because excessively high buckles increase intraretinal stress and can elevate the retina at the buckle edges. The result of excessive indentation is an increased risk in tears and redetachment. Conversely, too shallow-indentation results in an ineffective scleral buckling effect.

The present invention features novel eye shape modification (ESM) methods and systems. The eye shape modification (ESM) methods and systems of the present invention help provide modification of the globe via placement of a novel scleral buckle. Remodeling of the eye globe may help reduce biomechanical risk of retinal detachment, change refractive error, and/or prevent myopia progression. The methods and systems of the present invention may be safer and easier to surgically implant as compared to traditional scleral buckles.

Without wishing to limit the present invention to any theory or mechanism, it is believed that the methods and systems of the present invention are advantageous because the methods and systems provide the design of a calibrated system for eye shape modification (ESM), utilizes an ESM device to repair retinal detachments and reduce risk of a recurrent detachment, limits further horizontal or vertical expansion of the eye in myopia, and lengthens the eye in hyperopia.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features eye shape modification systems. In some embodiments, the system comprises a band having a first end, a second end opposite the first end, and a first side; a fixation zone disposed on the first side of the band, the fixation zone is adapted to accept sutures and is further adapted to be sutured to a scleral surface of an eye; and a calibrated shortening mechanism for tightening the band in increments.

In some embodiments, the fixation zone comprises a suture flange with apertures, arched loops, loops, T-shaped arms, bulbed T-shaped arms, bulbed finger extensions, or a combination thereof. In some embodiments, the fixation zone is attached to the band via an extension zone, the extension zone places the fixation zone a distance from the band. In some embodiments, the extension zone comprises an entrapment zone for trapping a suture passing through or around the fixation zone. In some embodiments, the entrapment zone comprises an indentation, a perforation, a slot, or a slit.

In some embodiments, the system further comprises a guide tip disposed on the first end of the band and an attachment loop disposed near the second end of the band, the guide tip can be threaded through the attachment loop.

In some embodiments, the calibrated shortening mechanism comprises an attachment zone positioned in between the guide tip and the fixation zone, the attachment zone comprises regions of narrowed width, the attachment zone allows for fixation with the attachment loop.

In some embodiments, the system further comprises a grasping projection for grasping the band while passing the band through the attachment loop.

In some embodiments, the system further comprises a closure system disposed on the band at or near the ends, the closure system is adapted to secure the band in place around an eye. In some embodiments, the closure system comprises a peg and hole loop closure system. In some embodiments, the closure system comprises a ridge and slot closure system. In some embodiments, the closure system comprises a tapered ridge and slot closure system wherein the ridges comprise bevels or tapers. In some embodiments, the closure system comprises a self-retaining loop closure system.

In some embodiments, the system further comprises a retention ring, wherein the ends of the band can be held together within the retention ring.

In some embodiments, the calibrated shortening mechanism comprises notches disposed along sides of the band, the notches are positioned at or near the ends of the band such that they overlap when the band is wrapped around an eye. In some embodiments, the notches are separated a distance apart, the distance being between about 250 µm to 5 mm.

In some embodiments, the system further comprises calibration lines molded into or marked on the band.

In some embodiments, the guide tip comprises a guide loop. In some embodiments, the guide tip comprises a tapered tip. In some embodiments, the tapered tip comprises a holding component, the holding component can accept a portion of forceps so as to stabilize attachment between the system and forceps.

The present invention also features methods of modifying eye shape. In some embodiments, the method comprises providing an eye shape modification (ESM) system of the present invention; placing the ESM system around an eye; joining the first end or a region near the first end and the second end or a region near the second end of the band; positioning the system such that the band lies flat on the eye; tightening the system via a calibrated tightening mechanism; and securing the system to the eye by suturing the fixation zone to the eye.

In some embodiments, the step of joining the first end or a region near the first end and the second end or a region near the second end of the band comprises: passing the ends through a retention ring, passing the ends through an O-ring, or passing a guide tip disposed at the first end of the band through an attachment loop disposed at the second end of the band.

DESCRIPTION OF PREFERRED EMBODIMENTS

Figure 1A:
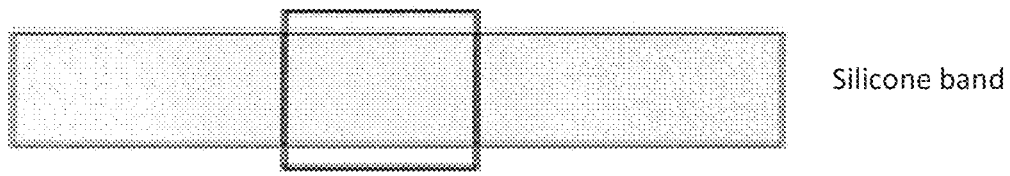
FIG. 1A is an example of a traditional scleral buckle and a schematic view of a horizontal mattress suture (prior art).

Following is a list of elements corresponding to a particular element referred to herein:
- 100 eye shape modification (ESM) system
- 110 band
- 111 first end of band
- 112 second end of band
- 113 first side of band
- 114 second side of band
- 120 fixation zone
- 122 extension zone 340
- 124 entrapment zone 350
- 130 suture flange
- 132 apertures
- 136 retention ring (136)
- 138 notches (138)
- 140 arched loop
- 142 loop
- 146 T-shaped arm
- 147 bulbed cross-shaped arm
- 148 bulbed T-shaped arm
- 149 bulbed finger extension
- 150 suture holes
- 160 guide tip
- 160a guide loop
- 160b tapered tip
- 161 holding component
- 162 attachment zones
- 164 grasping projection
- 168 attachment loop
- 170 calibration lines
- 180 closure system
- 181 pegs
- 182 holes
- 184 ridges
- 186 slots
- 190 retaining pegs
- 192 enlarged heads
- 194 retaining slots

600 arch portion
602 arm

Referring now to FIG. 1B-10, the present invention features novel eye shape modification (ESM) methods and systems.

The ESM system (100) comprises a band (110) (a scleral buckle) having a first end (111), a second end (112) opposite the first end (111), a first side (113), and a second side (114) opposite the first side (113). The band (110) is wrapped around the eye and the ends (111, 112) or regions around the ends (111, 112) are brought together.

Joining of the Ends of the Band

The ends (111, 112) may be brought together via a variety of mechanisms. For example, in some embodiments, the system (100) comprises a retention ring (136). FIG. 2B and FIG. 2C show a band (110) wrapped around an eye and the ends (111, 112) are held together via a retention ring (136). In some embodiments, the retention ring (136) is attached to the band (110). In some embodiments, the retention ring (136) is an independent ring. The retention ring (136) may also allow for calibrated shortening of the portion of the length of the band (110) around the eye.

Figure 4A:
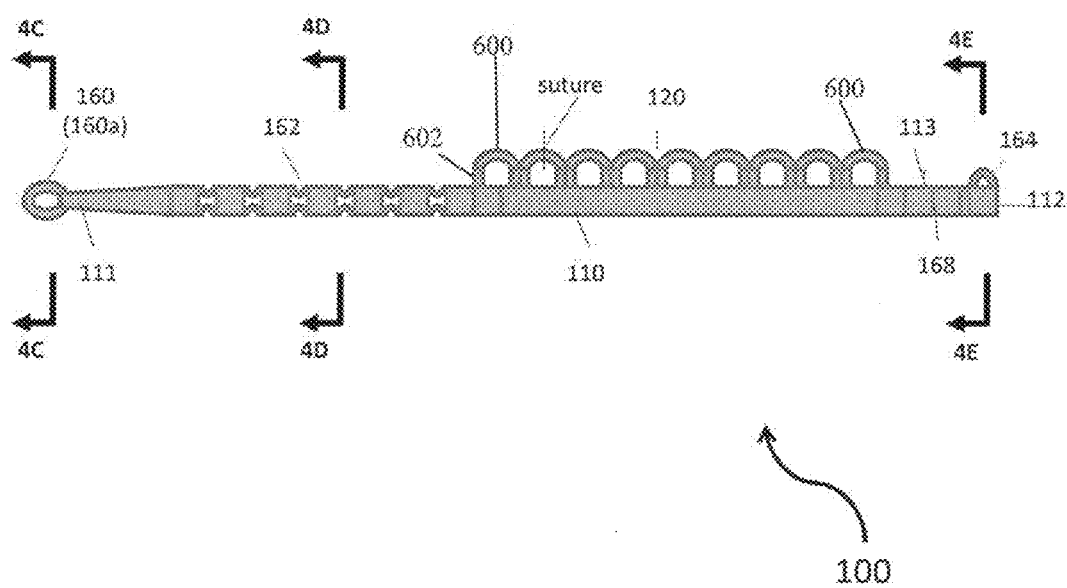
FIG. 4A is a top view of an embodiment of the systems of the present invention. The system comprises a guide tip and attachment loops, attachment zones, and fixation zones (e.g., with entrapment zones).
Figure 4B:
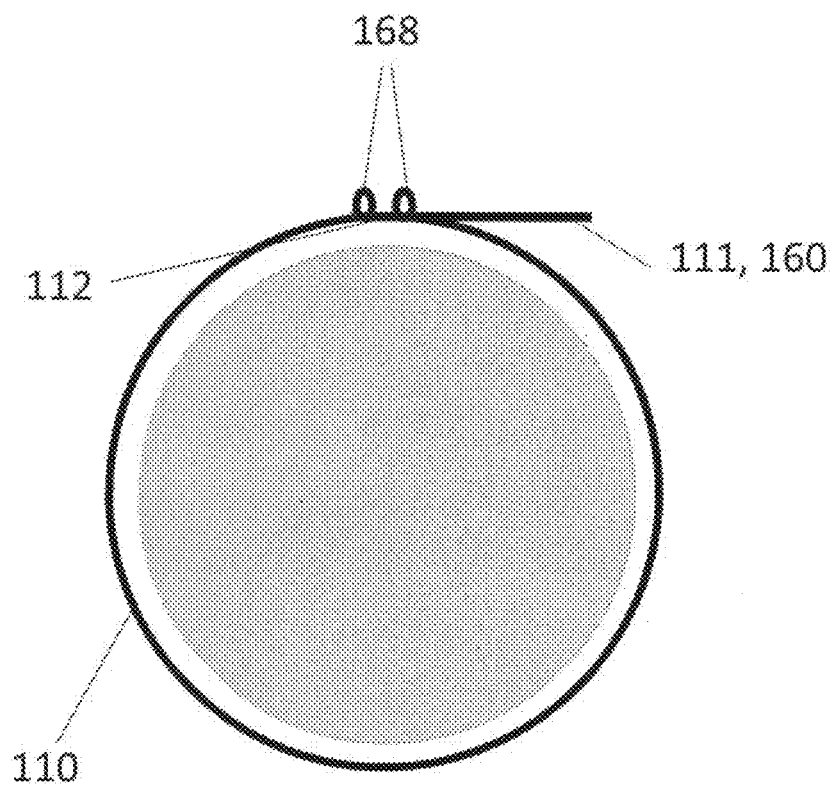
FIG. 4B is a side (in-use view) of the system of FIG. 4A (the features are not drawn to scale). The tip (the first end) is shown threaded through the attachment loops at the second end of the band.
Figure 4C:
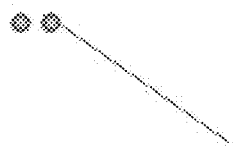
FIG. 4C is a cross sectional view of the guide tip of the system of FIG. 4A.
Figure 4D:
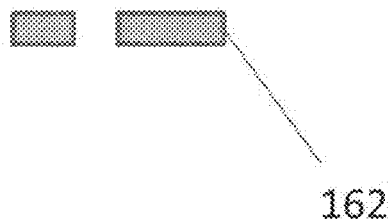
FIG. 4D is a cross sectional view of the attachment zone of the system of FIG. 4A.
Figure 4E:
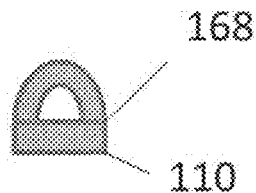
FIG. 4E is a cross sectional view of the attachment loop of the system of FIG. 4A.
Figure 4F:
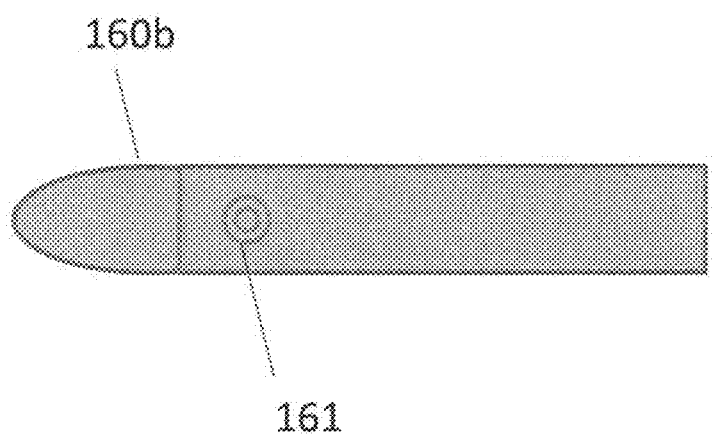
FIG. 4F is a top view of an embodiment of a guide tip of the system of the present invention.

In some embodiments, the ends (111, 112) are brought together via a tip and attachment loop mechanism. As shown in FIG. 4A-E, in some embodiments, the system (100), e.g., the band (110), comprises a guide tip (160), e.g., disposed at the first end (111) of the band (110). The guide tip (160) may be constructed in a variety of configurations. For example, in some embodiments, the guide tip (160) comprises a guide loop (160*a*) (see FIG. 4A). In some embodiments, the guide tip (160) comprises a tapered tip (160*b*) (see FIG. 4F). In some embodiments, the guide tip (160), e.g., guide loop (160*a*), may be grasped with a specific guide clamp or tied with a silk tie to allow for easy placement around the eye. FIG. 4C shows a cross sectional view of the guide tip (160), e.g., guide loop (160*a*), shown in FIG. 4A. FIG. 4F shows the guide tip (160) in the tapered tip (160*b*) configuration. The rounded tip may function as a pocket into which forceps or a probe may be placed to assist in pasting the system (100) under the rectus muscles and Tenon's capsule. In some embodiments, a holding component (161) is disposed in the tapered tip (160*b*). The holding component (161) can accept a rod (e.g., part of the forceps), e.g., to stabilize the attachment between the system (100) and the forceps. The holding component (161) may comprise any appropriate mechanism for gripping or holding the band (110), e.g., a perforation, a nub, a hole, a raised surface, a gripping surface, etc.).

In some embodiments, one or more (or a plurality) of attachment loops (168) are disposed on the band (110) at or near the second end (112). The guide tip (160) can pass through the attachment loop(s) (168). In some embodiments, the band (110) comprises one attachment loop (168). In some embodiments, the band (110) comprises two attachment loops (168). In some embodiments, the band (110) comprises more than two attachment loops (168). The attachment loops (168) are spaced a distance apart. For example, in some embodiments, the attachment loops (168) are spaced about 6 mm apart. In some embodiments, the band (110) may have a gradually increasing width that allows easy passage through attachment loops (168). FIG. 4E shows a side cross sectional view of the attachment loop (168) shown in FIG. 4A.

Fixation Zones

In some embodiments, the system (100) comprises a fixation zone (120) or a plurality of fixation zones (120) disposed on a side (113, 114) of the band (110). The fixation zones (120) are areas that can accept sutures; for example, the suture can attach the fixation zones (120) to the sclera. The fixation zones (120) are generally flexible and provide flexibility (e.g., slack) to allow the band (110) to be tightened without the sutures (sutures placed prior to tightening of the band) being pulled and distorting the band or scleral tissue. The fixation zones (120) may be constructed in a variety of configurations. In some embodiments, the fixation zones (120) are disposed within the band (110). Non-limiting examples are described below.

Figure 1B:
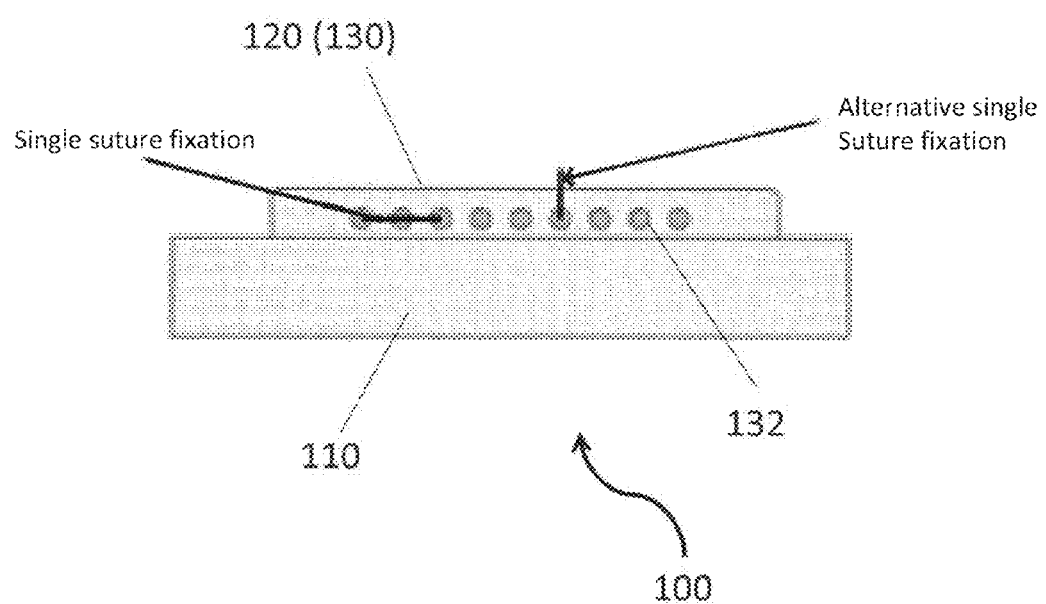
FIG. 1B is a top view (as laid atop the sclera) of an embodiment of the systems of the present invention.

As shown in FIG. 1B, in some embodiments, the fixation zone (120) comprises a suture flange (130). The suture flange (130) may extend outwardly from a side (e.g., 113, 114) of the band (110). In some embodiments, the suture flange (130) runs along at least a portion of the length of the band (110), the length of the band (110) referring to the first end to the second end. For example, in some embodiments, the suture flange (130) extends from the first end to the second end. In some embodiments, the suture flange (130) extends from near the first end to near the second end (see FIG. 1B). Disposed in the suture flange (130) is a plurality of apertures (132) (e.g., perforations). The apertures (132) are adapted to allow passage of sutures. For example, in some embodiments, a single suture is passed through a first aperture and a second aperture. In some embodiments, a single suture is passed through only a single aperture.

Figure 3A:
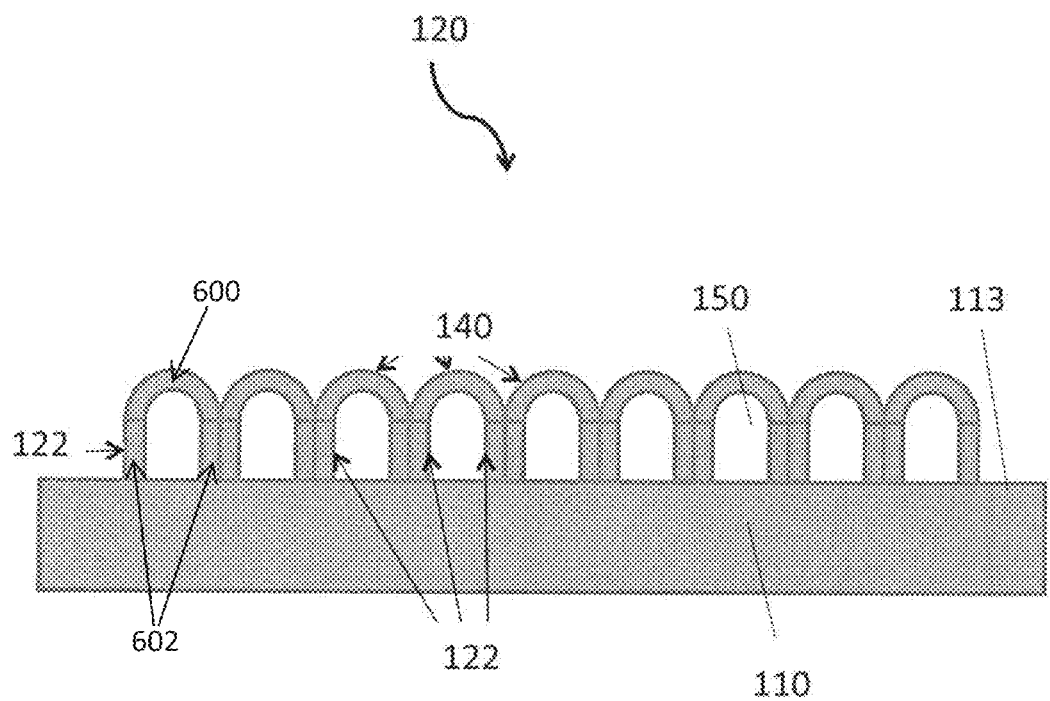
FIG. 3A is a top view of an embodiment of part of the systems of the present invention.
Figure 3B:
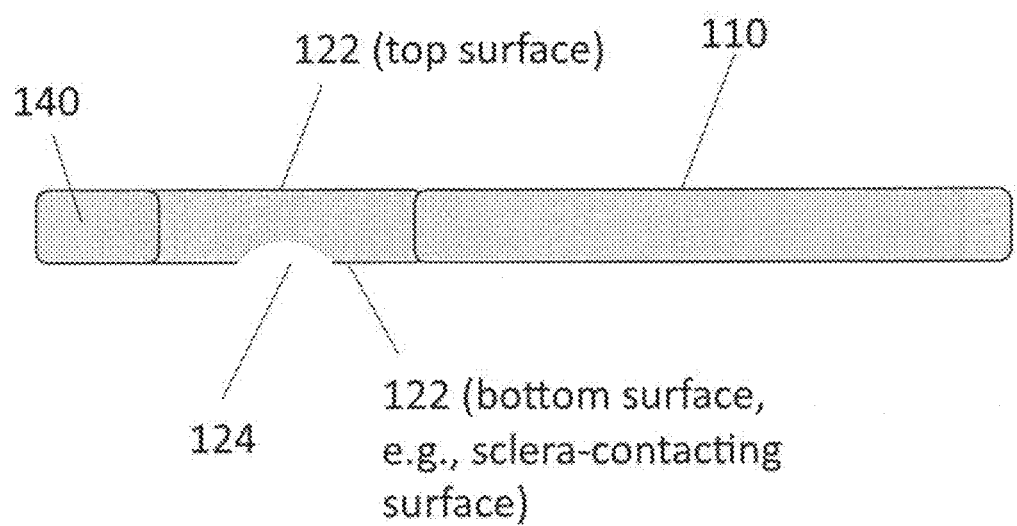
FIG. 3B is a side view of the components of FIG. 3A (e.g., the extension zone, the arched loop fixation zone, and the band). The entrapment zone cuts into the bottom surface of the extension zone (e.g., the surface that makes contact with the sclera). The entrapment zones are not limited to the positions and configurations shown and described herein.

As shown in FIG. 3A, in some embodiments, the fixation zones (120) comprise arched loops (140) extending from the band, effectively creating suture holes (150). Sutures may be placed within the suture holes (150) of the fixation zones (120) (e.g., arched loops (140)). The arched shape of the arched loops (140) may allow for the band (110) to stretch while helping to minimize distortion of the band (110) and helping to prevent circumferential traction on the sutures. The radius and the overall shape of the fixation zones (120) (e.g., arched loops (140)) may vary according to a desired spacing between the suture holes (150) within the fixation zones (120) (e.g., arched loops (140)). In some embodiments, the arch loop comprises an arch portion (600) and two arms (602) connected to the arch portion. The two arms connect to the band. In some embodiments, the stitching is at the location of the arch portion The fixation zones (120) may be directly attached to the band (110) or they may be attached to the band (110) via extension zones (122). The extension zones (122) place the fixation zones (120) (e.g., the arch of the arched loops (140)) a desired distance from the band (110). The extension zones (122) may also feature mechanisms for trapping the sutures, e.g., the suture ends that may otherwise erode through the conjunctiva. For example, as shown in FIG. 3B, in some embodiments, entrapment zones (124) are disposed in the extension zones (122). The entrapment zones (124) may be, for example, indentations, perforations, slots, or slits in the extension zones (122) that function to trap the suture.

Figure 3C:
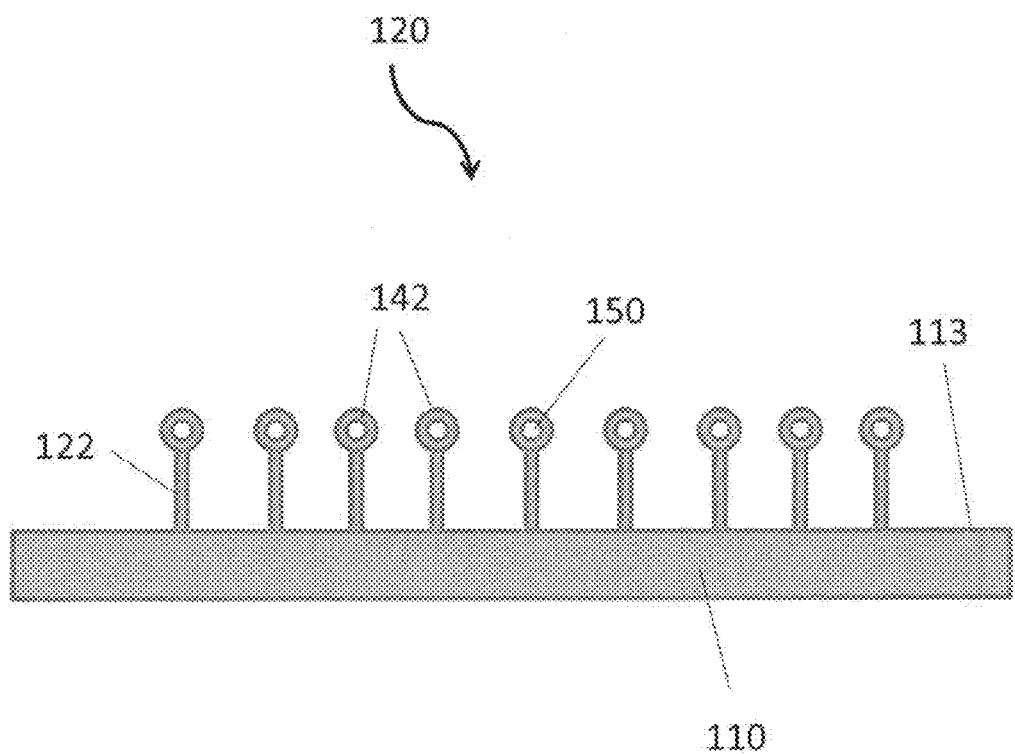
FIG. 3C is a top view of an embodiment of the systems of the present invention.

The fixation zones (120) are not limited to arched loops (140)). As shown in FIG. 3C, in some embodiments, the fixation zones (120) comprise loops (142). The loops (142) form suture holes (150) adapted to accept sutures. The sutures can fix the loops (142) to the sclera. In some embodiments, the loop (142) comprises an entrapment zone (124). The number of loops (and sizes) may vary.

Figure 3D:
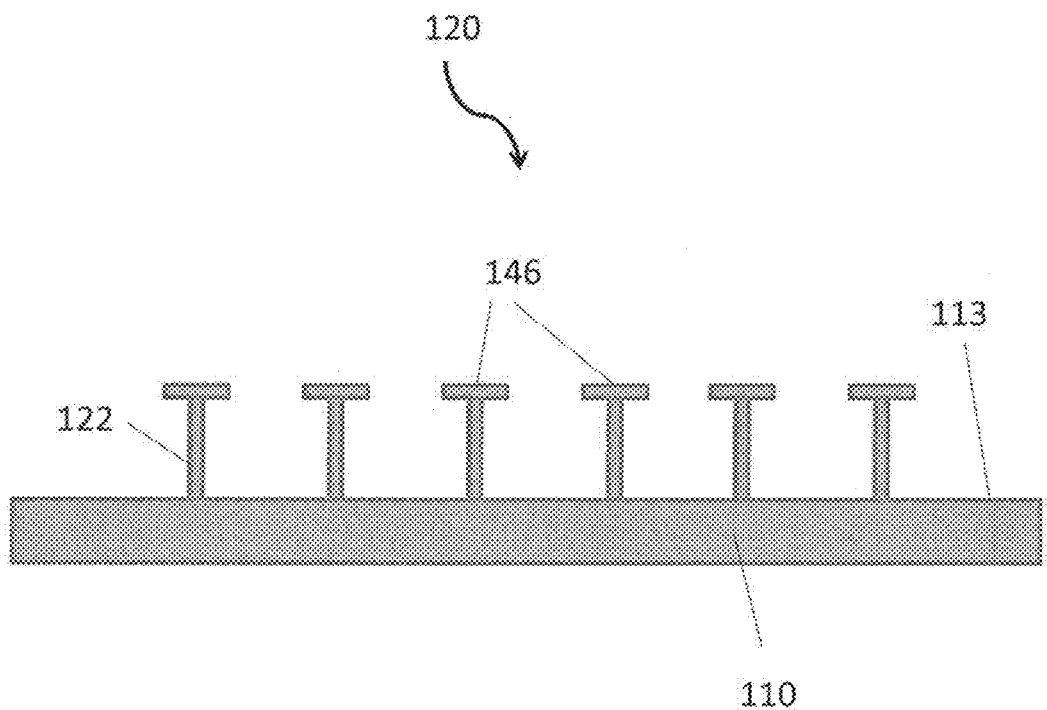
FIG. 3D is a top view of an embodiment of the systems of the present invention.

As shown in FIG. 3D, in some embodiments, the fixation zones (120) comprise a T-shaped arm (146). Sutures can attach the T-shaped arm (146) to the sclera. In some embodiments, the T-shaped arm (146) comprises an entrapment zone (124). The number of T-shaped arms (146) (and sizes) may vary.

Figure 3E:
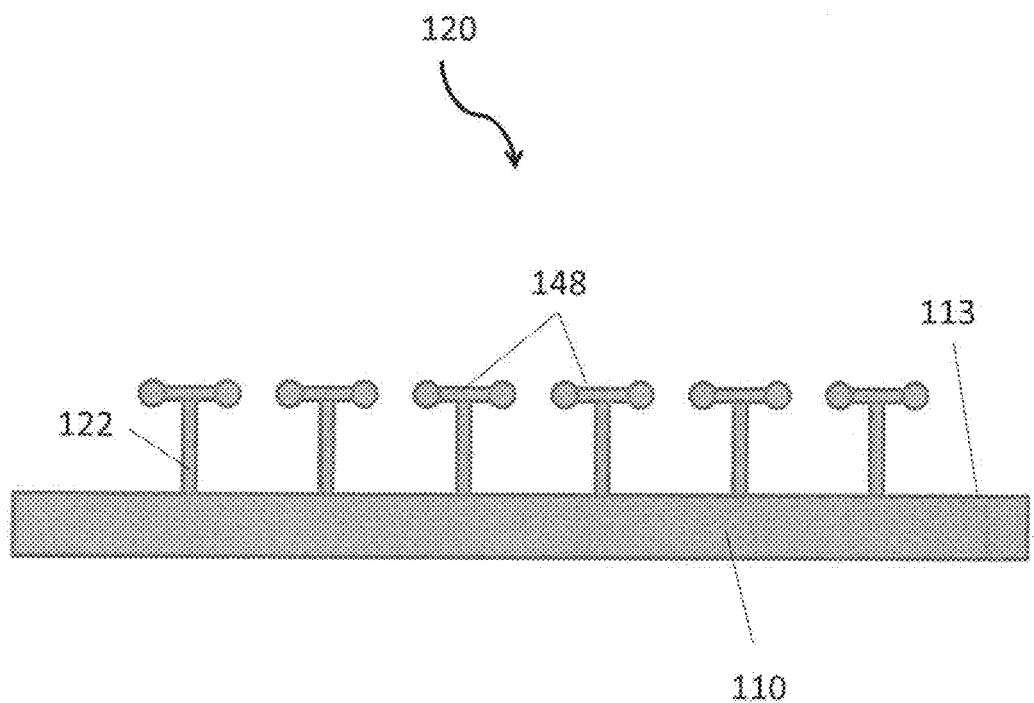
FIG. 3E is a top view of an embodiment of the systems of the present invention.

As shown in FIG. 3E, in some embodiments, the fixation zones (120) comprise a bulbed T-shaped arm (148) (e.g., a T-shaped arm with rounded ends on the ends of the T-shaped arm). Sutures can attach the bulbed T-shaped arm (148) to the sclera. In some embodiments, the bulbed T-shaped arm (148) comprises an entrapment zone (124). The number of bulbed T-shaped arms (148) (and sizes) may vary.

Figure 3F:
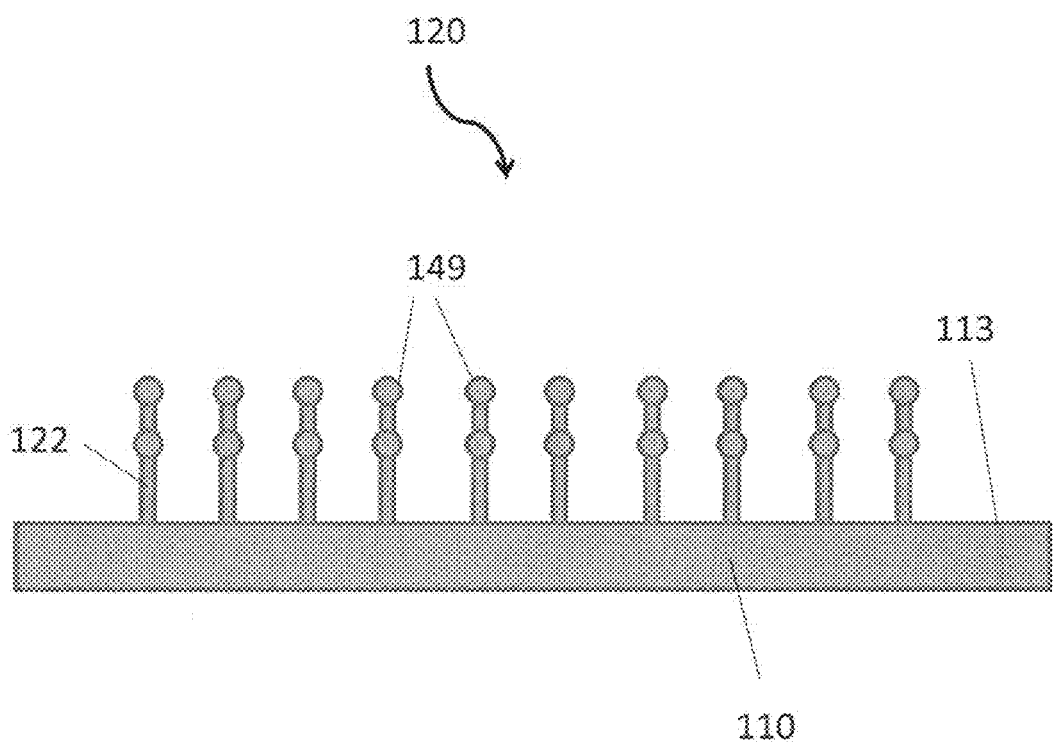
FIG. 3F is a top view of an embodiment of the systems of the present invention.

As shown in FIG. 3F, in some embodiments, the fixation zones (120) comprise bulbed finger extensions (149). Sutures can attach the bulbed finger extensions (149) to the sclera, e.g., the area between bulbs. In some embodiments, the bulbed finger extensions (149) comprise entrapment zones (124). The number of bulbed T finger extensions (149) (and sizes) may vary.

Figure 3G:
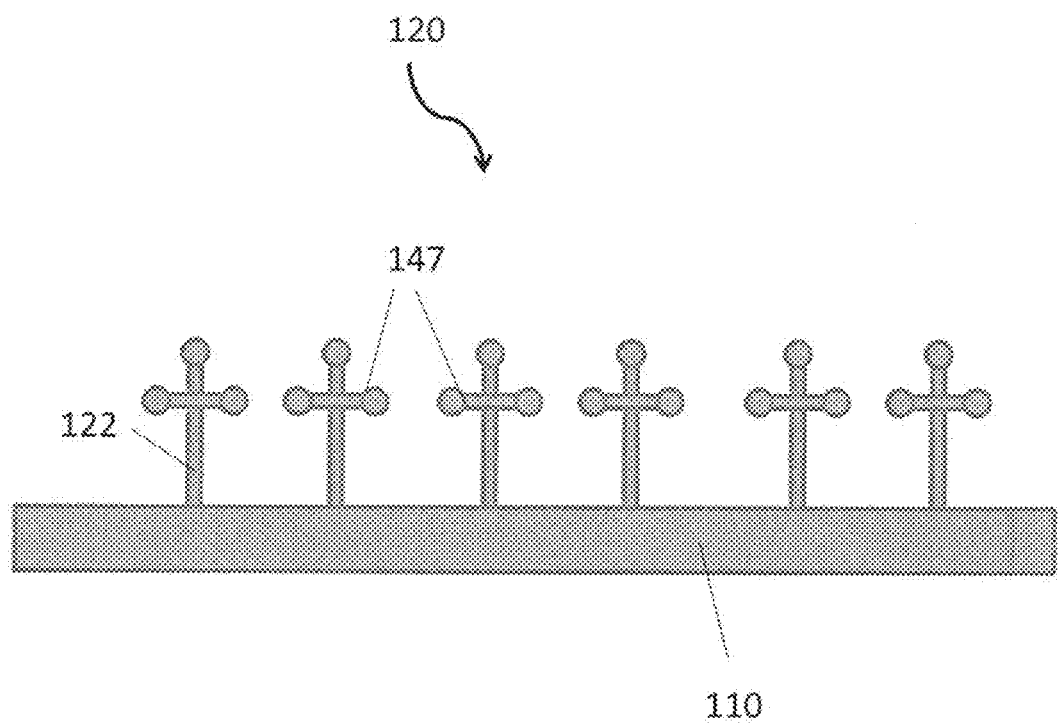
FIG. 3G is a top view of an embodiment of the systems of the present invention.

As shown in FIG. 3G, in some embodiments, the fixation zones (120) comprise bulbed cross-shaped arms (147). Sutures can attach the bulbed cross-shaped arms (147) to the sclera, e.g., the area between bulbs. In some embodiments, the bulbed cross-shaped arms (147) comprise entrapment zones (124). The number of bulbed cross-shaped arms (147) (and sizes) may vary.

The length of the extension zones (120) may vary. For example, in some embodiments, the extension zones (120) are between about 0.1 to 2 mm in length (e.g., from the band (110) to the fixation zones (120)). In some embodiments, the extension zones (120) are between about 1 to 4 mm in length (e.g., from the band (110) to the fixation zones (120)). In some embodiments, the extension zones (120) are between about 2 to 5 mm in length (e.g., from the band (110) to the fixation zones (120)). In some embodiments, the extension zones (120) are between about 3 to 8 mm in length (e.g., from the band (110) to the fixation zones (120)). The extension zones (120) are not limited to the aforementioned lengths.

Calibrated placement of an ESM system (100) of the present invention may be possible with a singular or plurality of sutures per quadrant. In some embodiments, once the distance of the retinal tear or location of the equator (maximum diameter of the eye) from the limbus is measured, an ESM system (100) of the present invention may be placed at the retinal break or desired location with fixation sutures placed, e.g., at an appropriate and/or convenient distance posterior to the limbus (e.g., about 5-8 mm posterior to the limbus), making installation of an ESM easy and convenient. In some embodiments, the extension zone is long, e.g., 1.5 cm from the band; this allows placement of a convenient anterior fixation suture but indentation of the ESM at a more posterior location. Differences in individual geometry can be accommodated in this fashion.

In some embodiments, the band (110) comprises a grasping projection (164). The grasping projection (164) makes grasping the band (110) easily while passing the band (110) (e.g., the guide tip (160)) through the attachment loops (168). In some embodiments, the grasping projection (164) is a loop. In some embodiments, the grasping projections (164) comprise a tab or other appropriate component for grasping the band (110).

In some embodiments, the system comprises perforations disposed in the band (110). The perforations may allow placement of a suture or other material (e.g., a polymer peg) through aligned perforations to allow fixation to the sclera.

Calibrated Shortening Mechanism

In some embodiments, the system (100) comprises a calibrated tightening mechanism (or calibrated shortening mechanism) for allowing the band (110) to be tightening in increments (e.g., small increments). This can help the surgeon determine how much he/she is tightening the band (110) and/or how much the eye is being manipulated. Calibrated shortening or tightening of the band (110) of the system (100) may be achieved by any appropriate mechanism. In some embodiments, the calibrated shortening mechanism may be either vertical or horizontal regional narrowing of the system (e.g., the band). Non-limiting examples of calibrated shortening mechanisms are described below.

In some embodiments, the calibrated shortening mechanism comprises attachment zones (162) disposed in the band (110). The attachment zones (162) shown in FIG. 4A have regions of narrowed width to allow fixation with the attachment loops (168) at the opposite end of the band (110). FIG. 4D shows a cross sectional view of the attachment zone (162) shown in FIG. 4A.

In some embodiments, the calibrated shortening mechanism comprises notches (138) disposed along the sides (113, 114) of the band (110). The notches (138) may be positioned at or near the ends (111, 112) of the band (110) such that they overlap when the band (110) is wrapped around the eye. In some embodiments, when the band (110) is wrapped around the eye, the notches (138) allow the two ends to be attached (e.g., via retention ring (136)) and then adjusted in preset increments (e.g., between about 500 µm to 1 mm). This may allow for controlled modification of the ocular diameter and globe shape.

In some embodiments, the notches (138) (e.g., the deepest point of the notches) are separated a distance apart. In some embodiments, the distance is between about 250 µm to 5 mm. In some embodiments, the distance is between about 750 µm to 5 mm. The distance is not limited to the aforementioned examples.

Closure System

Figure 5:
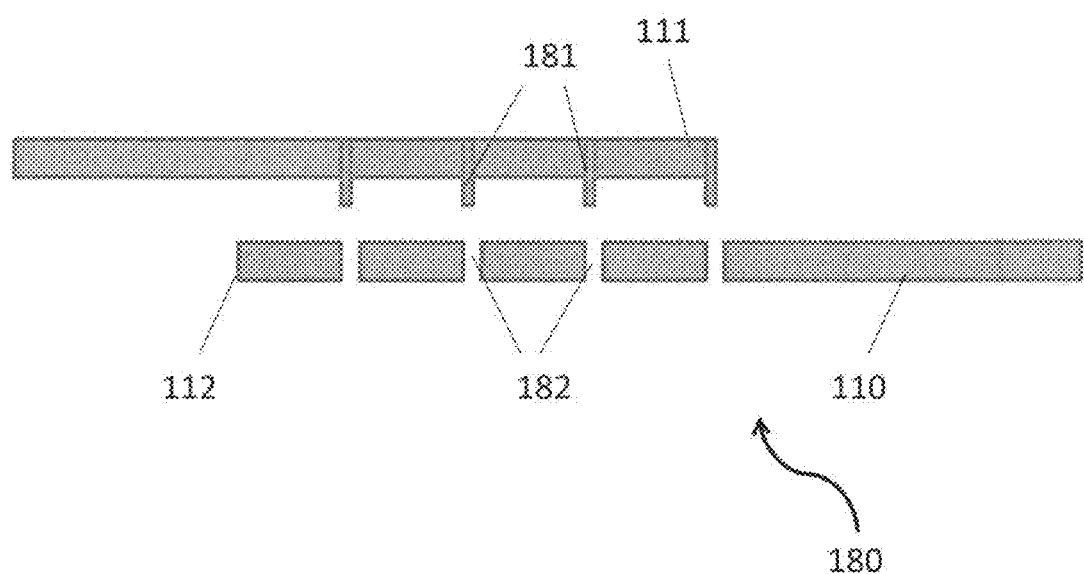
FIG. 5 is a side (cross sectional) view of an embodiment of the systems of the present invention. The view of the band is as if the band were wrapped around the eye. Disposed on the band is a peg and hole loop closure mechanism.

As shown in FIG. 5-8, in some embodiments, the system (100) comprises a closure system (180) for helping to secure the ends (111, 112) of the band (110) together, e.g., once the band (110) has been wrapped around the eye and the ends (111, 112) are joined via attachment loops (168), a retention ring (136), etc. The closure system (180) may be disposed at or near the ends (111, 112) of the band (110). FIG. 5 shows an example of a peg and hole loop closure system. Pegs (181) (tabs, flanges, etc.) extend outwardly from a surface (e.g., top or bottom surface) of the band (110) at or near the first end (111) of the band (110), and holes (182) are accordingly disposed (e.g., top or bottom surface) at or near the second end (112) of the band (110). The pegs and holes are adapted to engage each other and secure the ends (111, 112) of the band (110). For example, when the band (110) is wrapped around the eye, the pegs (181) can be inserted into the holes (182). The pegs (181) and holes (182) may be placed distances apart from one another, respectively, according to a physician, manufacturer, etc. The spacing of the closure system (100) (e.g., pegs and holes, etc.) may help the surgeon determine how much the band (110) is being tightened.

Figure 6:
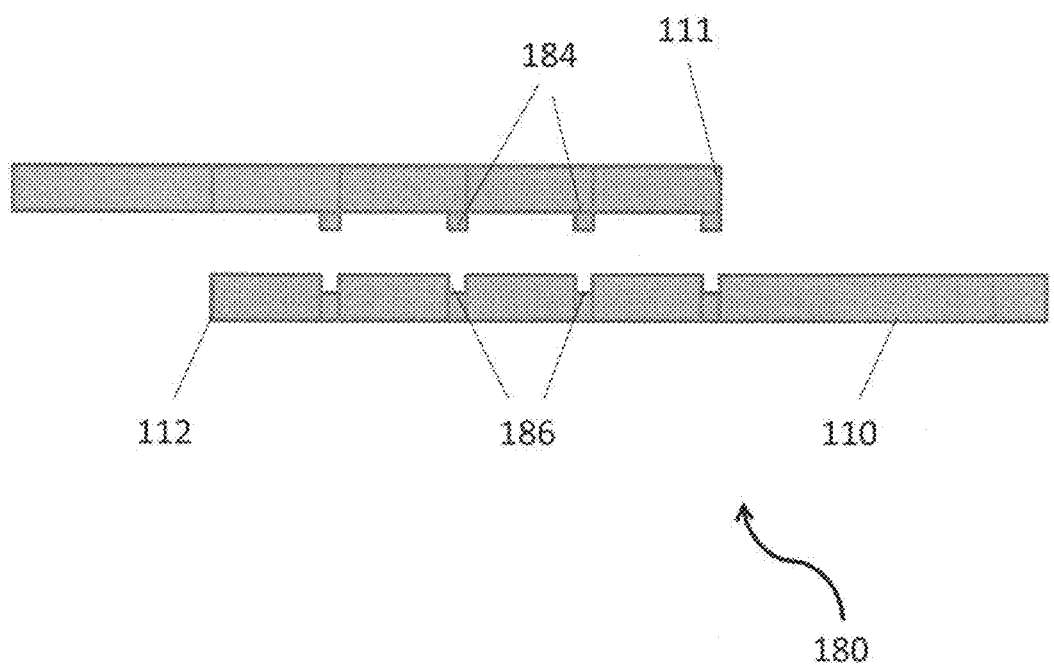
FIG. 6 is a side view of an embodiment of the systems of the present invention. The view of the band is as if the band were wrapped around the eye. Disposed on the band is a ridge and slot closure mechanism.
Figure 7:
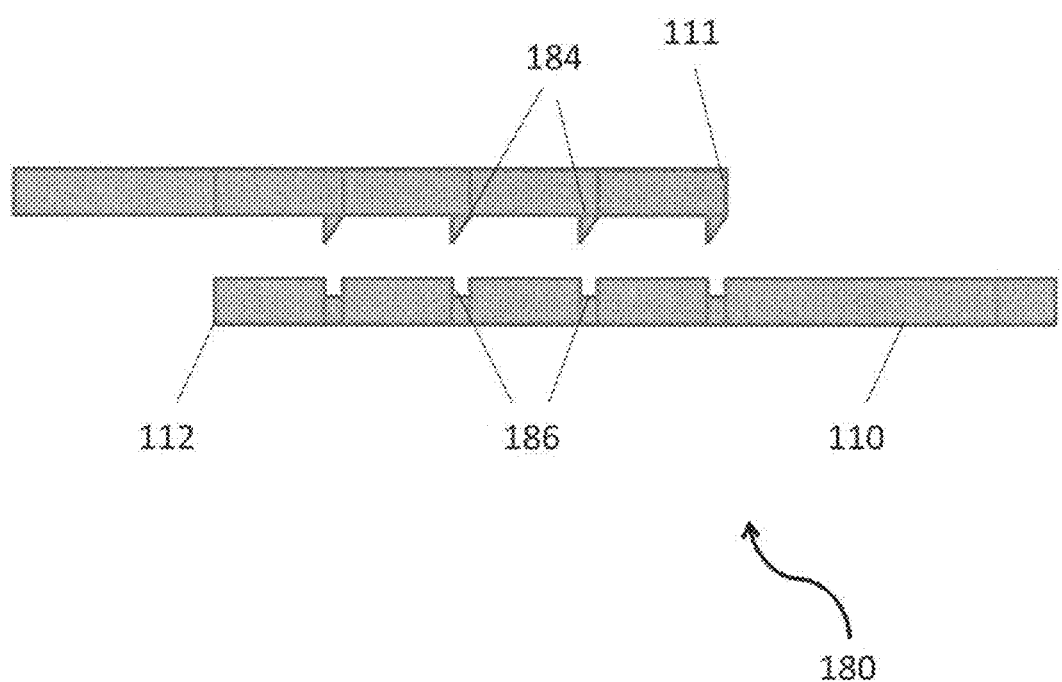
FIG. 7 is a side view of an embodiment of the systems of the present invention. The view of the band is as if the band were wrapped around the eye. Disposed on the band is a tapered ridge and slot closure mechanism.

Likewise, in FIG. 6, in some embodiments, the closure system (180) comprises a ridge and slot closure system. In some embodiments, ridges (184) extend outwardly from a surface of the band (110) at or near the first end (111) of the band (110), and slots (186) are accordingly disposed at or near the second end (112) of the band (110). The ridges (184) and slots (186) are adapted to engage each other and secure the band (110) in place. For example, when the band (110) is wrapped around the eye, the ridges (184) can be inserted into the slots (186). The ridges (184) and slots (186) may be placed distances apart from one another, respectively, according to a physician, manufacturer, etc. As shown in FIG. 7, in some embodiments, the closure system (180) comprises a tapered ridge and slot closure system. The tapered ridge and slot closure system is similar to the ridge and slot closure system of FIG. 6. In the tapered ridge and slot closure system, the ridges (184) comprise bevels or tapers as shown.

Figure 8:
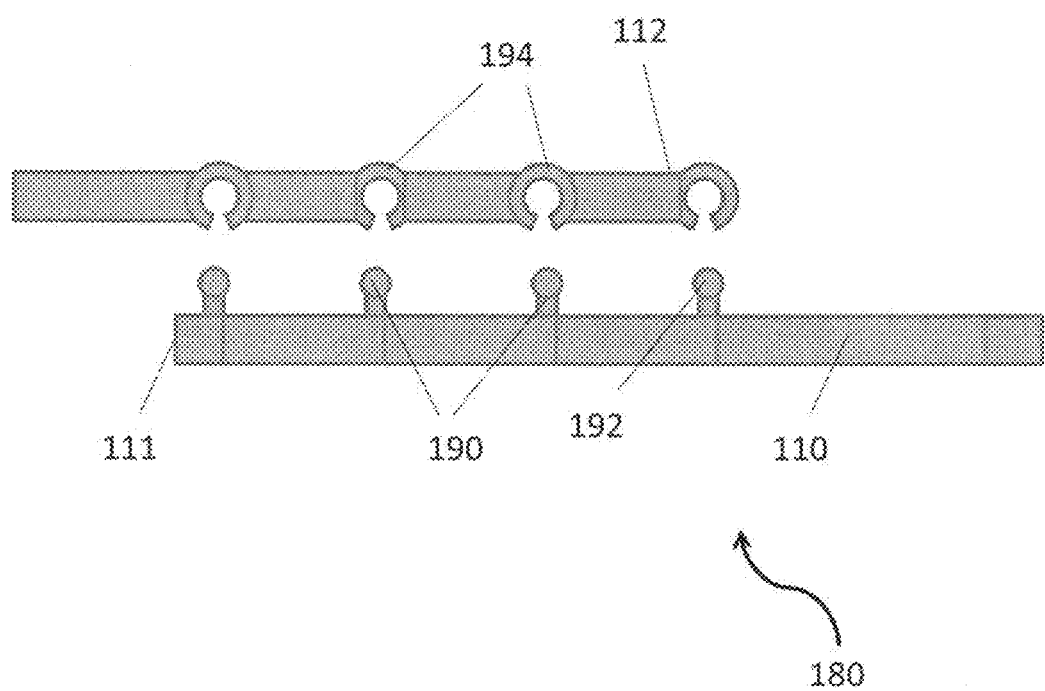
FIG. 8 is a side (cross sectional) view of an embodiment of the systems of the present invention. The view of the band is as if the band were wrapped around the eye. Disposed on the band is a self-retaining loop closure mechanism.

As shown in FIG. 8 in some embodiments, the closure system (180) comprises a self-retaining loop closure system. In some embodiments, retaining pegs (190) with enlarged heads (192) (e.g., spherical heads on a cylindrical or rectangular peg) extend outwardly from a surface of the band (110) at or near the first end (111) of the band (110). Retaining slots (194) are accordingly disposed at or near the second end (112) of the band (110). The retaining slots (194) have an inner cavity and a narrowed opening. The retaining peg (190/192) is forced into the inner cavity of the retaining slot (194) through the narrowed opening and can remain within the retaining slot (194) until pulled back through the narrowed opening. The retaining pegs (190) and retaining slots (194) are adapted to engage each other and secure the band (110) in place. For example, when the band (110) is wrapped around the eye, the retaining pegs (190) can be inserted into the retaining slots (194). The retaining pegs (190) and retaining slots (194) may be placed distances apart from one another, respectively, according to a physician, manufacturer, etc.

The present invention is not limited to the aforementioned closure systems (180) for closing and/or securing the ESM system (100). For example, in some embodiments, adhesive may be used to affix the two ends (111, 112) of the ESM system (100) together. In some embodiments, heat may be applied to the two ends of the ESM system (100) to fuse them together. In some embodiments, a loop of heat-shrink or cold-shrink memory polymers may be used to join the two ends (111, 112) of the ESM system (100). In some embodiments, polymer tack or a staple may be used to attach the two ends (111, 112) of the ESM system (100) together.

Figure 9:
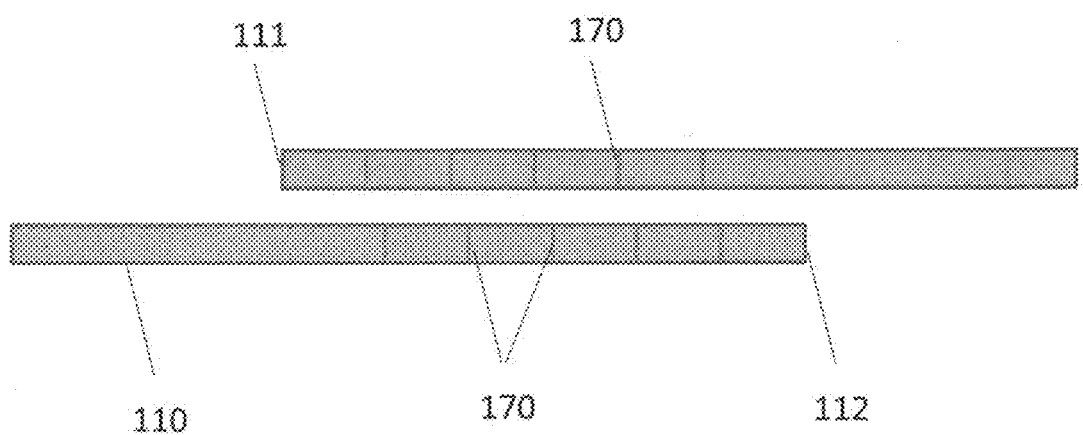
FIG. 9 is a side view of an embodiment of the systems of the present invention. The view of the band is as if the band were wrapped around the eye. Disposed on the band are calibration lines in attachment zones set at known distances.
Figure 10A:
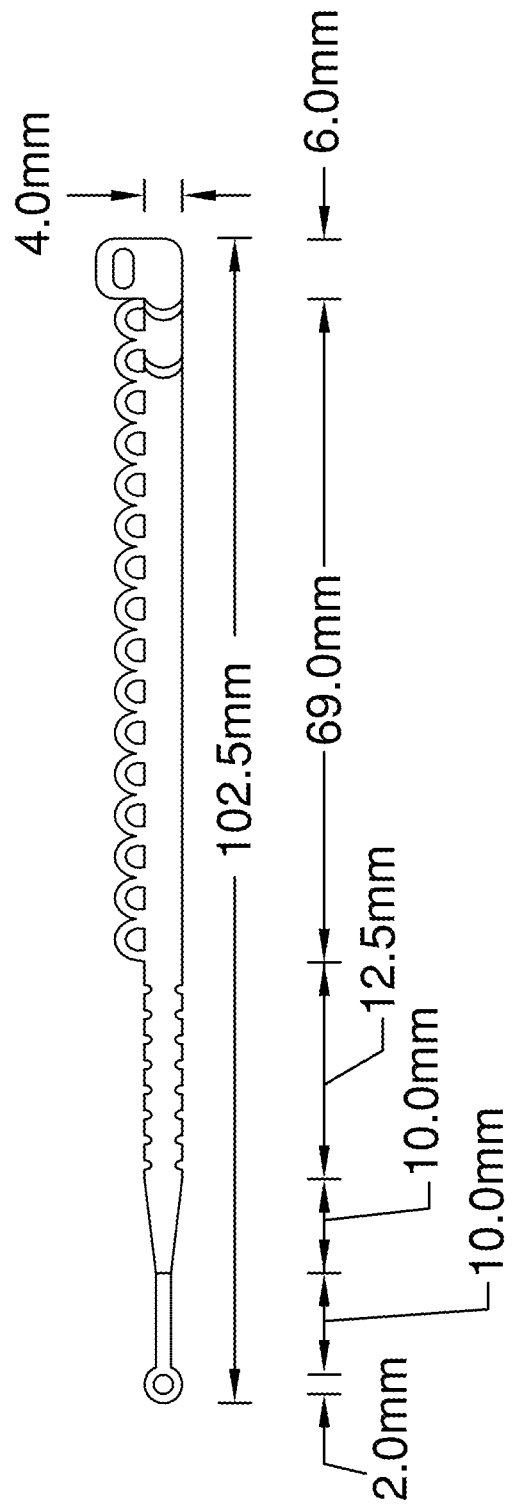
FIG. 10A shows examples of dimensions of the system of FIG. 4A. The present invention is not limited to the dimensions described herein.
Figure 10B:
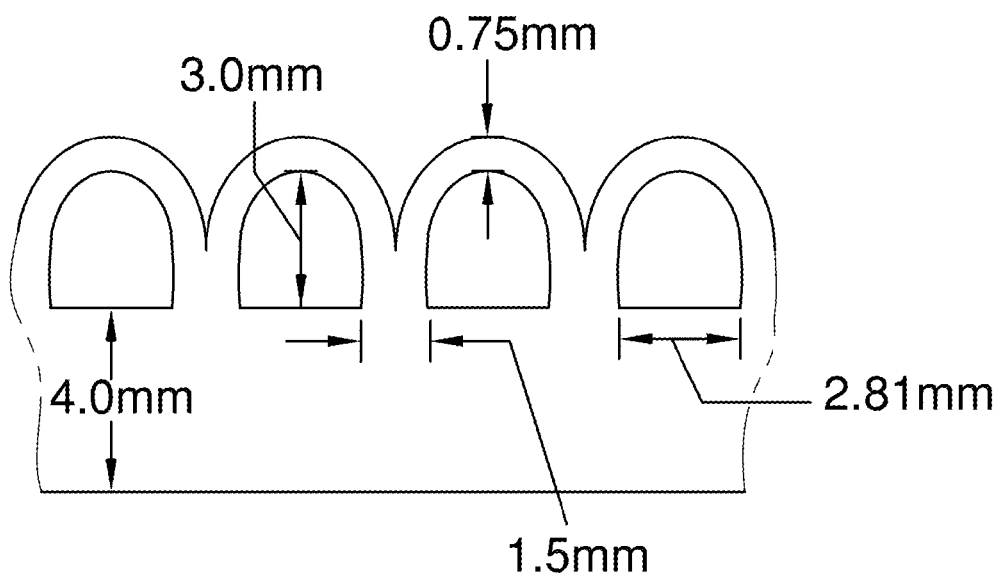
FIG. 10B shows examples of dimensions of the fixation zone of the system of FIG. 4A. The present invention is not limited to the dimensions described herein.
Figure 10C:
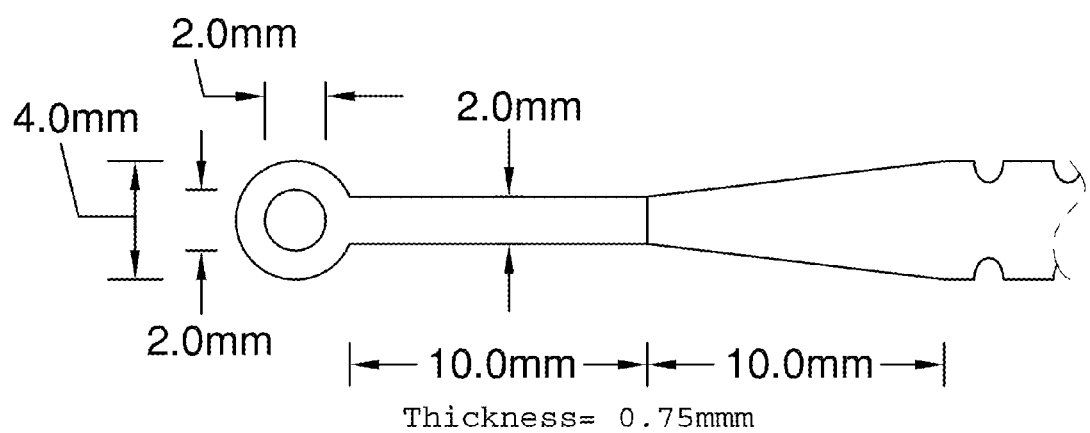
FIG. 10C shows examples of dimensions of the tip of the system of FIG. 4A. The present invention is not limited to the dimensions described herein.
Figure 10D:
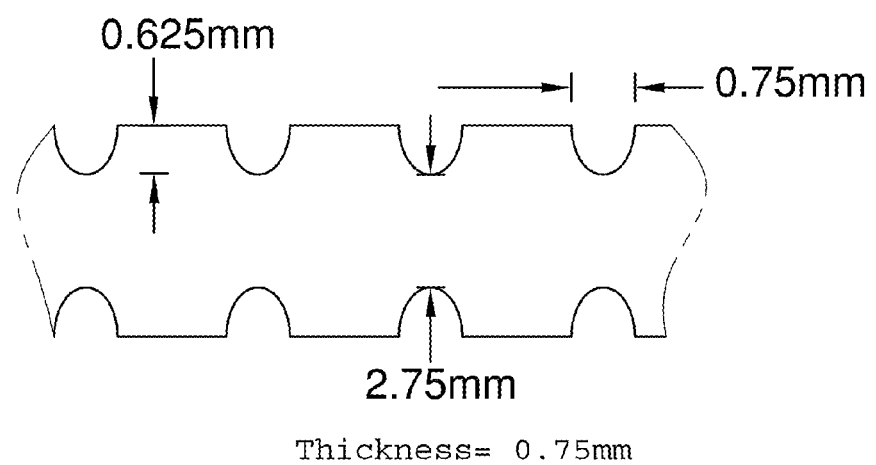
FIG. 10D shows examples of dimensions of the attachment zone of the system of FIG. 4A. The present invention is not limited to the dimensions described herein.
Figure 10E:
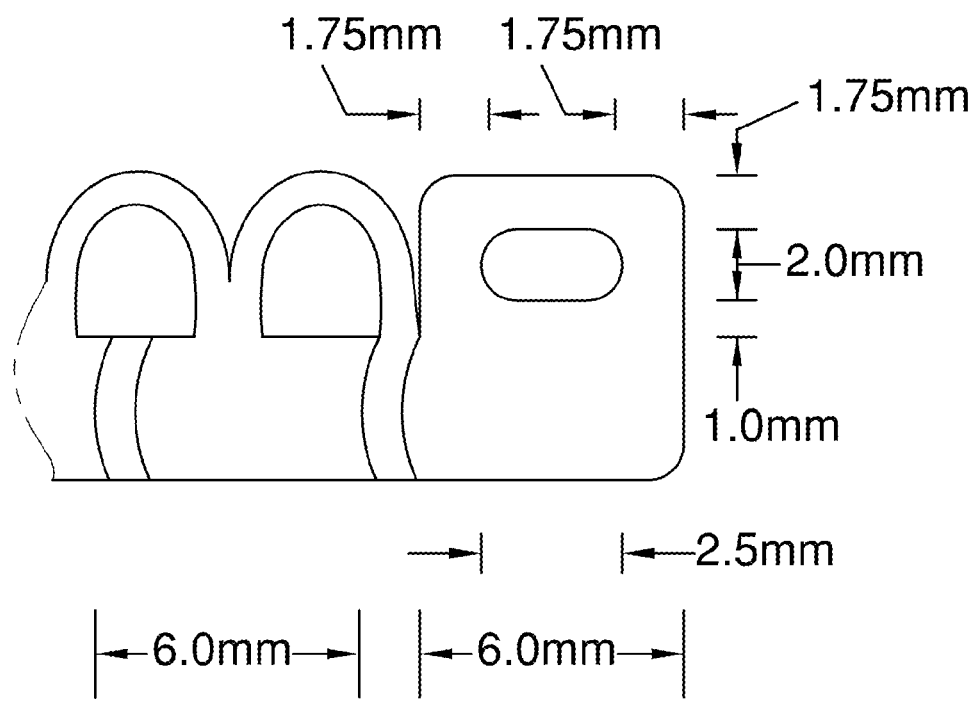
FIG. 10E shows examples of dimensions of the attachment loops and guide loop of the system of FIG. 4A. The present invention is not limited to the dimensions described herein.

As shown in FIG. 9, in some embodiments, the band (110) comprises a plurality of calibration lines (170) (e.g., measurement lines) disposed (e.g., molded into, marked on) in the band (110) at or near its ends (111, 112), e.g., at attachment zones at or near the ends (111, 112). The calibration lines (170) may be separated by a distance, e.g., as desired by the physician, manufacturer, etc. The calibration lines (170) may help the surgeon determine how much he/she is tightening the band (110). Other types of calibration mechanisms may be employed, for example a peg and hole mechanism, a hook and loop mechanism, a groove and tongue mechanism, the like, or a combination thereof.

FIG. 10 shows non-limiting examples of dimensions of the system (100) of the present invention. The dimensions of the systems (100) are not limited to those described herein. For example, FIG. 10 shows an example of the thickness of the band (110) as being about 0.75 mm. However, in some embodiments, the thickness of the band (110) is about 1 mm, about 2 mm, about 3 mm, about 4 mm, about 5 mm, about 6 mm, about 7 mm, etc.

The ESM system (100), e.g., band (110), may be constructed from a variety of materials. For example, in some embodiments, ESM system (100), e.g., band (110), is constructed from a material comprising silicone. The ESM system (100), e.g., band (110), of the present invention is not limited to silicone.

The ESM system may be used to entrap traditional scleral buckle elements against the eye as well. For example, scleral buckle elements designed to geometrically fit with the ESM may be placed under the ESM to allow fixation against the sclera.

EXAMPLE 1

Surgical Procedure of a Traditional Scleral Buckle

Example 1 is an example of a traditional scleral buckle procedure.

The eye is prepped and draped in the usual surgical fashion, and a lid speculum is placed between the eyelids to keep the eye open. ¾ cm horizontal incisions are made in the conjunctiva at the 3:00 and 9:00 positions. The conjunctiva is then incised circumferentially at the limbus in a peritomy fashion. The Tenon's capsule is then dissected from the underlying scleral bed with tenotomy scissors. Each rectus muscle is then isolated with a 2-0 silk tie. The sclera is inspected for thinning. The retina is examined under indirect ophthalmoscopy and the location of the retinal tear is identified by indenting the sclera over the retinal tear with a depressor. The sclera over the tear is then marked with an inked skin marker. The retinal tear is treated with cryotherapy or laser photocoagulation.

At this time, the globe is retracted using the silk ties to turn the globe to give adequate exposure and a horizontal mattress suture of 5-0 nylon or polypropylene is placed in 2 passes, each parallel to the limbus. A section of the encircling band or sclera buckle element may be used to place the sutures in the desired location with adequate separation of the passes to allow entrapment of the element or band.

The encircling band +/− element is placed under the preplaced sutures and under the four rectus muscles. The ends of the encircling band are attached with a loop of silicone rubber. Drainage of subretinal fluid through pars plane vitrectomy or external drainage and gas injection is done next if appropriate.

The preplaced sutures are tied, locked, and rotated posteriorly to decrease risk of erosion of the sclera. The encircling band is tightened until the desired amount of indentation is achieved. The ends of the encircling band are trimmed. The Tenon's capsule and conjunctiva are reapproximated using resorbable suture.

EXAMPLE 2

Surgical Procedure Using Scleral Buckles of the Present Invention

Figure 2A:
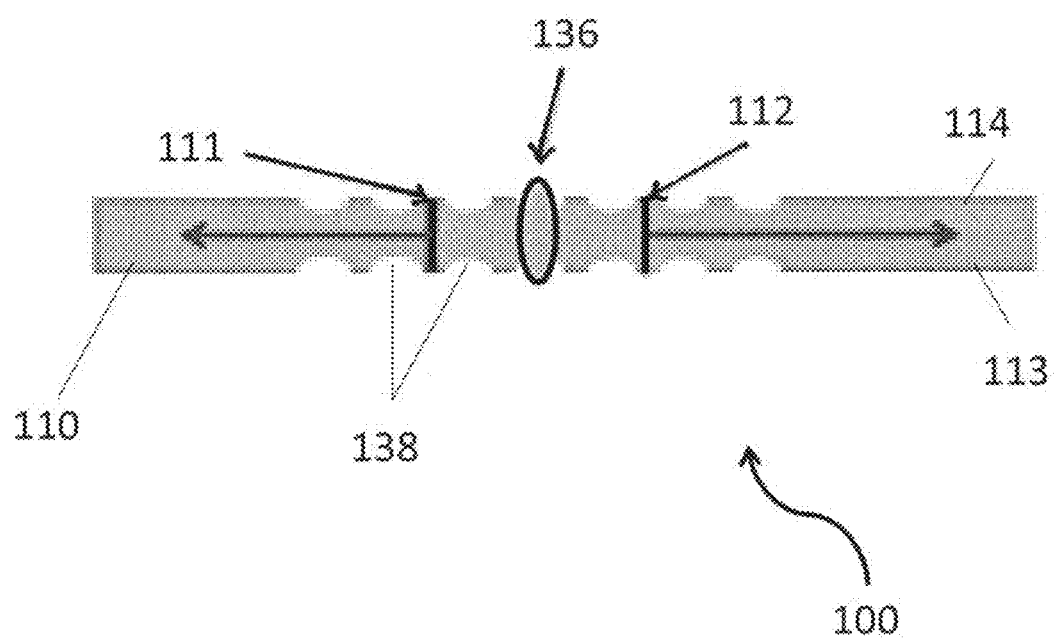
FIG. 2A is a top view (as laid atop the sclera) of an embodiment of the systems of the present invention. The view of the band is as if the band were wrapped around the eye. The free ends are held together via the retention ring.
Figure 2B:
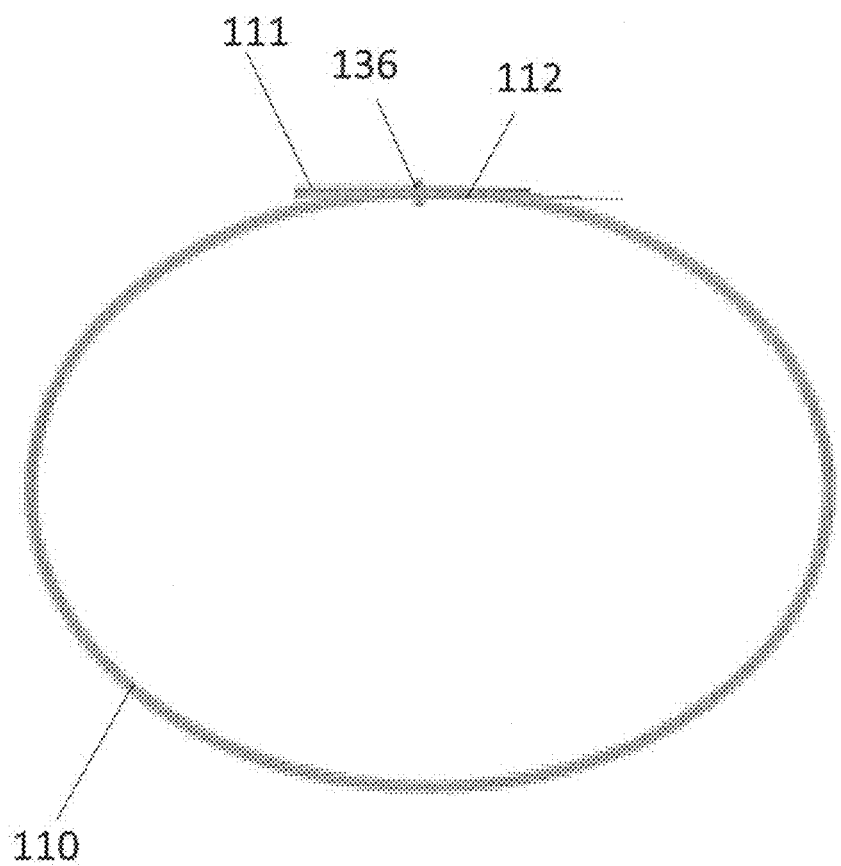
FIG. 2B is a side cross sectional view of the system of FIG. 2A, e.g.; as if the band were wrapped around the eye. The free ends of the band are held together via the retention ring. The second end is positioned below the first end of the belt (and the ends are clipped).
Figure 2C:
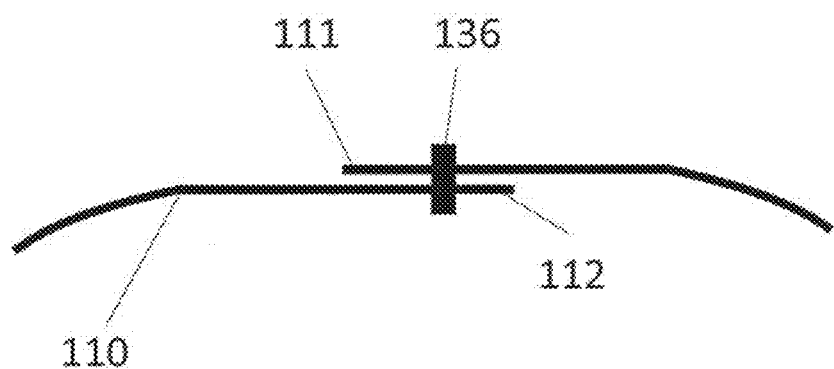
FIG. 2C is a detailed view of the system of FIG. 2B, wherein the second end is positioned below the first end of the belt (and the ends are clipped).

Example 2 is a non-limiting example of a novel surgical procedure according to the systems and methods of the present invention (e.g., in FIG. 2 and/or FIG. 9). The methods of the present invention are not limited to the steps described herein.

The eye is prepped and draped in the usual surgical fashion and a lid speculum is placed between the eyelids to keep the eye open ¾ cm horizontal incisions are made in the conjunctiva at the 3:00 and 9:00 positions. The conjunctiva is then incised circumferentially at the limbus in a peritomy fashion. The Tenon's capsule is then dissected from the underlying scleral bed with tenotomy scissors. Each rectus muscle is then isolated with a 2-0 silk tie. The sclera is inspected for thinning. The retina is examined under indirect ophthalmoscopy and the location of the retinal tear is identified by indenting the sclera over the retinal tear with a depressor. The sclera over the tear is then marked with an inked skin marker. The retinal tear is treated with cryotherapy or laser photocoagulation.

At this time, the globe is retracted using the silk ties to turn the globe to give adequate exposure and a horizontal mattress suture of 5-0 nylon or polypropylene is placed in 2 passes, each parallel to the limbus. A section of the encircling band or scleral buckle element may be used to place the sutures in the desired location with adequate separation of the passes to allow entrapment of the element or band.

The encircling band +/− element is placed under the preplaced sutures and under the 4 rectus muscles. The ends of the encircling band are attached with a loop of silicone rubber. Drainage of subretinal fluid through pars plana vitrectomy or external drainage and gas injection is done next if appropriate.

The preplaced sutures are tied, locked, and rotated posteriorly to decrease risk of erosion of the sclera. The encircling band is tightened until the desired amount of indentation is achieved by using the calibration lines or counting the number of notches tightened. The ends of the encircling band are trimmed. The Tenon's capsule and conjunctiva are reapproximated using resorbable suture.

EXAMPLE 3

Surgical Procedure Using Scleral Buckles of the Present Invention

Example 3 is a non-limiting example of a novel surgical procedure according to the systems and methods of the present invention (e.g., in FIG. 3 and/or FIG. 4). The methods of the present invention are not limited to the steps described herein.

The eye is prepped and draped in the usual surgical fashion and a lid speculum is placed between the eyelids to keep the eye open ¾ cm horizontal incisions are made in the conjunctiva at the 3:00 and 9:00 positions. The conjunctiva is then incised circumferentially at the limbus in a peritomy fashion. The Tenon's capsule is then dissected from the underlying scleral bed with tenotomy scissors. Each rectus muscle is then isolated with a 2-0 silk tie. The sclera is inspected for thinning. The retina is examined under indirect ophthalmoscopy and the location of the retinal tear is identified by indenting the sclera over the retinal tear with a depressor. The sclera over the posterior edge of the retinal tear is then marked with an inked skin marker. The retinal tear is treated with cryotherapy or laser photocoagulation.

At this time, the distance from the limbus to the posterior edge of the retinal tear is measured. The anterior-posterior (AP) dimension of the ESM is subtracted from the distance to the posterior edge of retinal tear to give the distance from the limbus that the fixation suture must be placed. For example, if the retinal tear is 16 mm posterior to the limbus and the AP dimension of the ESM is 7 mm, the mark would be at 9 mm posterior to the limbus.

The globe is retracted using the silk ties to turn the globe to give adequate exposure and a 5-0 nylon or polypropylene suture is placed at the marked location. No posterior suture is passed and minimal retraction is necessary.

The ESM is placed under the 4 rectus muscles. The ends of the encircling band are attached with a loop of silicone rubber so that the ESM lies flat but not taut against the eye. The preplaced sutures are passed through the perforations (for type ESM in FIG. 1B) or through fixation zone ESM in FIG. 3 or 4 (for type Drainage of subretinal fluid through pars plana vitrectomy or external drainage and gas injection is done next if appropriate.

The preplaced sutures are tied, locked, and rotated posteriorly to decrease risk of erosion of the sclera. The ends of the suture are placed through under the retention zones. The tip of the ESM is placed through the attachment loops of the ESM. The ESM is tightened one unit at a time until the desired amount of indentation is achieved. The end of the ESM is trimmed. The Tenon's capsule and conjunctiva are reapproximated using resorbable suture.

EXAMPLE 4

Surgical Procedure Using Scleral Buckles of the Present Invention

Example 4 is a non-limiting example of a novel surgical procedure according to the systems and methods of the present invention (e.g., FIG. 3 and/or FIG. 4 with minimal incision approach). The methods of the present invention are not limited to the steps described herein.

The eye is prepped and draped in the usual surgical fashion and a lid speculum is placed in the eye. The conjunctiva is incised radially in each of the 4 oblique quadrants using a blunt Wescott scissor. Instead of the usual 360 conjunctival peritomy that is performed in scleral buckle surgery, the incision is made at least 5 mm posterior to the limbus. The Tenon's capsule is then incised. The location of the ora serrata (corresponds to the muscle insertion point) is marked with a marking pen. That is the location of the muscle insertions and leaves the anterior conjunctiva intact (e.g., much less invasive and safer for the cornea). The incisions are made extended as far posteriorly as the surgeon feels is required for good exposure.

The peripheral retina is examined under sclera depression and indirect ophthalmoscopy. The sclera over the posterior edge of the retinal tear is marked with a novel scleral marker, one that allows marking without the manipulation required using current techniques. The retinal tear is treated with cryoretinopexy or laser photocoagulation in the usual fashion.

The distance from the initial marking point to the retinal break is measured and an ESM system of the present invention that will cover the break is selected for installation. A single suture or multiple sutures are placed at the initial marking point in each quadrant. The ESM system is placed under each of the rectus muscles and is sutured into place using the preplaced sutures. The sutures are tied, locked, and rotated posteriorly. The suture ends are tucked under the retention zones.

Drainage of subretinal fluid through pars plane vitrectomy or external drainage and gas injection is done next if appropriate. The ESM system may be joined with an O-ring or passed through the attachment loops and adjusted until the ESM system lies flat on the globe surface but does not indent it. Next, the ESM system is tightened in a calibrated fashion. Upon completion of the ESM system implantation, the conjunctiva is reapproximated using absorbable suture and cautery. Much less manipulation and incision is required using an ESM rather than a traditional scleral buckle procedure.

As used herein, the term "about" refers to plus or minus 10% of the referenced number.

The disclosures of the following U.S. patents are incorporated in their entirety by reference herein: U.S. Pat. No. 5,529,076; U.S. Pat. No. 4,549,529; U.S. Pat. No. 4,851,003; U.S. Pat. No. 5,188,125; U.S. Pat. No. 4,976,719; U.S. Pat. No. 7,037,336; U.S. Pat. No. 5,489,299; U.S. Pat. No. 4,549,529; U.S. Pat. No. 7,037,336; U.S. Pat. No. 5,354,331; U.S. Pat. No. 6,511,508; U.S. Pat. No. 7,316,676; U.S. Pat. No. 6,117,170; U.S. Pat. No. 4,907,586; U.S. Pat. No. 7,736,389; U.S. Pat. No. 4,961,744; U.S. Pat. No. 6,547,714; U.S. Pat. No. 5,503,165; U.S. Pat. No. 4,880,017; U.S. Pat. No. 5,722,952; U.S. Pat. No. 5,006,123; U.S. Pat. No. 5,300,118.

Various modifications of the invention, addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An eye shape modification system (100) for treating rhegmatogenous retinal detachment (RRD), the system comprising:
   (a) a scleral buckle (110) having a tapered first end (111), a second end (112) opposite the first end (111), a first side (113), and a second side (114) opposite the first side (113), wherein the scleral buckle (110) is adapted to be wrapped around the eye and the ends (111, 112) are brought and held together;
   a guide tip (160) disposed on the first end (111) of the scleral buckle (110) and a plurality of attachment loops (168) disposed adjacent the second end (112) of the scleral buckle (110), the guide tip (160) can be threaded through the attachment loop (168);
   (b) a fixation zone (120) disposed on the first side (113) of the scleral buckle (110), the fixation zone (120) is adapted to accept sutures and is further adapted to be sutured to a scleral surface of an eye;
   (c) a calibrated shortening mechanism for tightening the scleral buckle (110) in increments; and
   (d) a closure system (180) disposed on the scleral buckle (110) at or near the ends (111, 112), the closure system (180) is adapted to secure the scleral buckle (180) in place around an eye,
   wherein the fixation zone (120) is positioned between the plurality of attachment loops (168) and the first end (111) of the scleral buckle (110), the fixation zone (120) comprising a suture flange (130) extending outwardly from the first side (113) of the scleral buckle (110), the suture flange (130) comprising a plurality of arched loops (140) each defining a suture hole (150) in order to attach the scleral buckle (110) to the sclera using sutures,
   wherein the calibrated shortening mechanism comprises an attachment zone (162) positioned in between the guide tip (160) and the fixation zone (120), the attachment zone (162) comprises regions of narrowed width, the attachment zone (162) allows for fixation with the attachment loop (168) at the opposite end of the scleral buckle (110) and for calibrated tightening of the scleral buckle (110) in small increments once the guide tip (160) is threaded through the attachment loops (168).

2. The system (100) of claim 1, wherein the fixation zone (120) is attached to the scleral buckle (110) via an extension zone (122), the extension zone (122) places the fixation zone (120) a distance from the scleral buckle (110).

3. The system (100) of claim 2, wherein the extension zone (122) comprises an entrapment zone (124) for trapping a suture passing through or around the fixation zone (120).

4. The system (100) of claim 3, wherein the entrapment zone (124) comprises an indentation, a perforation, a slot, or a slit.

5. The system (100) of claim 1 further comprising a grasping projection (164) at the second end (112) of the scleral buckle (110) for grasping the scleral buckle (110) while passing the scleral buckle (110) through the attachment loop (168).

6. The system (100) of claim 1, wherein the closure system (180) comprises a peg and hole loop closure system.

7. The system (100) of claim 1, wherein the closure system (180) comprises a ridge and slot closure system.

8. The system (100) of claim 1, wherein the closure system (180) comprises a tapered ridge and slot closure system wherein the ridges comprise bevels or tapers.

9. The system (100) of claim 1, wherein the closure system (180) comprises a self-retaining loop closure system.

10. The system (100) of claim 1 further comprising a retention ring (136), wherein the ends (111, 112) of the scleral buckle (110) can be held together within the retention ring (136).

11. The system (100) of claim 1 further comprising calibration lines (170) molded into or marked on the scleral buckle (110).

12. The system (100) of claim 1, wherein the guide tip (160) comprises a guide loop (160a).

13. The system (100) of claim 1, wherein the guide tip (160) comprises a tapered tip (160b).

14. The system (100) of claim 13, wherein the tapered tip (160b) comprises a holding component (161), the holding component (161) can accept a portion of forceps so as to stabilize attachment between the system (100) and forceps.

* * * * *